United States Patent [19]

Smith et al.

[11] Patent Number: 5,194,528
[45] Date of Patent: Mar. 16, 1993

[54] DIMER REDUCTION

[75] Inventors: Brian H. A. Smith, Sarnia; Melvin K. Allison, Wyoming, both of Canada

[73] Assignee: Polysar Limited, Sarnia, Canada

[21] Appl. No.: 369,068

[22] Filed: Jun. 20, 1989

[51] Int. Cl.$^5$ .......................... C08F 4/34; C08F 16/36
[52] U.S. Cl. .................................. 526/77; 526/232.1; 526/316
[58] Field of Search .......................................... 526/77

[56] References Cited

U.S. PATENT DOCUMENTS 2,851,497  9/1958  Stearns et al. .
3,009,005  11/1961 Schaffel .
4,134,811  1/1979  De Poortere et al. ............... 428/482
4,758,639  7/1988  Koyanagi et al. .................... 526/201

FOREIGN PATENT DOCUMENTS 1000000  11/1976  Canada .

OTHER PUBLICATIONS

Chemical Abstracts vol. 98, 1983 No. 98:82425c "Multilayer Interconnecting Structure".
Chemical Abstracts vol. 100, No. 100:219136r "Dry Photochemical Etching for Pattern Formation".
Chemical Abstracts vol. 101, 1984 No. 101:46307n "Negative-type Photoresist".
David M. Wiles, "Polymerization of Alpha-Beta-Unsaturated Carbonyl Compounds" pp. 223-281 from *Structure and Mechanism in Vinyl Polymerization* 1969.

*Primary Examiner*—Joseph L. Schofer
*Assistant Examiner*—Tom Weber
*Attorney, Agent, or Firm*—Stevens, Davis, Miller & Mosher

[57] ABSTRACT

The dimer content in alpha, beta- ethylenically unsaturated ketones may be reduced by treating the ketone with a peroxide of the formula

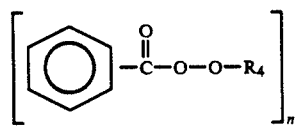

wherein $R_4$ is a $C_{1-6}$ branched or straight chain alkyl radical or a $C_{6-10}$ aromatic radical and n is 1 or 2. The treated ketone has a faster rate of polymerization with other ethylenically unsaturated monomers.

19 Claims, 4 Drawing Sheets

DIMER REDUCTION

FIELD OF THE INVENTION

The present invention relates to a process for treating solutions of ketone monomers which contain an ethylenic unsaturation alpha, beta to the carbonyl group. More particularly the present invention relates to a process for reducing the dimer content in such ketones.

BACKGROUND OF THE INVENTION

Ketones with an ethylenic unsatuation alpha beta to the carbonyl group have a number of uses. The utility of these monomers is based on the activation of the carbonyl group by ultraviolet radiation.

Such ketones may be used in photoresist applications such as making microcircuits. For example methyl isopropenyl ketone (3-methyl-3-butene-2-one) or MIPK is useful in photoresist applications as disclosed in:
CA 98:82425c of Japanese Kokai 57,159,045;
CA 100:219136r of Japanese Kokai 58,39,779., and
CA 101:46307n of Japanese Kokai 58,52,634.

Such ketone monomers are also useful in the manufacture of photodegradable plastics as disclosed in Canadian Patent 1,000,000 granted Nov. 16, 1976 to James E. Guillet and Harvey Troth.

Specific ketone monomers are useful in other applications. For example MIPK may be used in the production of isoprene as disclosed in U.S. Pat. No. 3,009,005 issued Nov. 14, 1961.

Unforunately, these ketones tend to form dimers. It is believed that the monomers undergo cyclodimerization. For example MIPK would be expected to form a 2,3-dihydropyran derivative. These dimers are an impurity and should be removed. Furthermore, in cases where the ketone is subjected to free radical polymerization, the dimers act as inhibitors. While it is possible to overcome the inhibiting effect of the dimer by using additional initiator this results in a lower molecular weight polymer which is undesirable and also more expensive.

U.S. Pat. No. 2,851,497 teaches that such dimers may be converted to the monomer by treating the dimer in a vapour phase at a temperature of at least 375°, preferably 420° to 520° C. While this may be an effective way of reducing or removing dimer, it is energy and capital intensive, and possibly dangerous.

The present invention seeks to provide a simple method to "reduce" such dimers. In accordance with the invention the dimer is not physically removed from the monomer but is believed to be converted to a different innocuous species. The decrease in dimer content may be monitored using conventional analytical procedures, such as chromatography.

SUMMARY OF THE INVENTION

The present invention provides a method for reducing the dimer content in a liquid mixture consisting essentially of:
one or more monomers of the formula

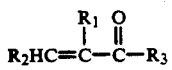

wherein
$R_1$ is a hydrogen atom or a $C_{1-4}$ alkyl radical;
$R_2$ is a hydrogen atom or a $C_{1-4}$ alkyl radical; and
$R_3$ is a $C_{1-4}$ alkyl radical or a $C_{6-10}$ aromatic radical; and
dimers thereof;
which comprises contacting said mixture with at least one or more peroxides selected from the group consisting of:
(i) benzoyl peroxide; and
(ii) peroxides of the formula

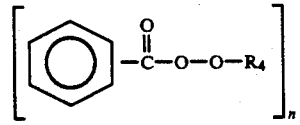

wherein $R_4$ is a $C_{1-6}$ branched or straight chain alkyl radical or a $C_{6-10}$ aromatic radical and n is 1 or 2, at a temperature and for a period of time so that the weight percent of a residual dimer in said mixture is reduced by at least 20 percent.

The present invention also provides a process comprising homopolymerizing the treated ketone or copolymerizing the treated ketone with one or more copolymerizable monomers.

DETAILED DESCRIPTION

Figure 1:
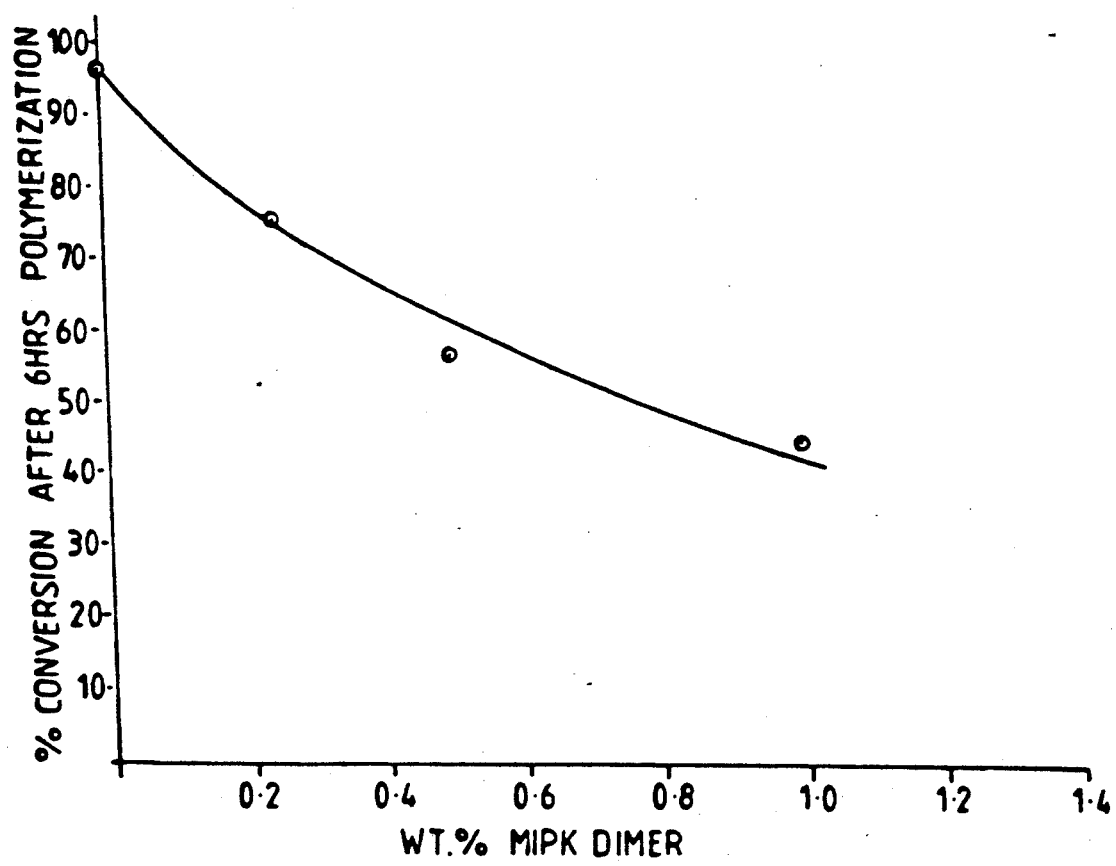
FIG. 1 is a plot showing the effect of MIPK dimer concentration on the polymerization of styrene.

The ketones which may be treated in accordance with the present invention are of the formula

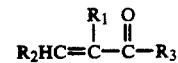

wherein:
$R_1$ is a hydrogen atom or a $C_{1-4}$ alkyl radical;
$R_2$ is a hydrogen atom or a $C_{1-4}$ alkyl radical; and
$R_3$ is a $C_{1-4}$ alkyl radical or a $C_{6-10}$ aromatic radical.

Some ketones which come within the above formula are methyl vinyl ketone (MVK), ethyl vinyl ketone, propyl vinyl ketone, isopropyl vinyl ketone, butyl vinyl ketone, methyl isopropenyl ketone (MIPK), ethyl isopropenyl ketone, phenyl vinyl ketone and phenyl isopropenyl ketone. Preferred ketones are methyl vinyl ketone and methyl isopropenyl ketone. Generally the ketones contain, in addition to the dimer, up to a maximum 4 to 5 preferably less than 2 weight percent of other ingredients such as inhibitors and other ketones. On aging at a temperature above the freezing point of the ketone, preferably above about 0° C. the dimer is formed. When received the dimer content may range anywhere from a minimum of 0.3 to up to 18 weight percent. Typically the dimer concentration is greater than 3 weight percent and thus should be reduced by at least 20 percent based on the weight of dimer in the ketone before treatment preferably to as low as practically possible before use.

The peroxide or peroxy esters useful in accordance with the present invention are benzoyl peroxide and peroxides of the formula:

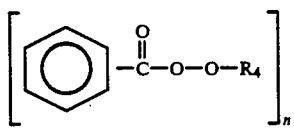

wherein $R_4$ is a $C_{1-6}$ branched or straight chain alkyl radical or a $C_{6-10}$ aromatic radical; and n is 1 or 2.

Useful peroxides include benzoyl peroxide and 2,5-dimethyl-2,5-bis(benzoyl peroxy) hexane. A particularly useful peroxide is benzoyl peroxide. These peroxides may contain up to 20 or 25 weight percent water. Care should be taken if the peroxides are used at low temperatures to avoid phase separation and/or ice formation.

In accordance with the present invention the peroxide is added to the ketone and the resulting mixture is aged at a temperature and for a time so that the residual dimer content in said ketone mixture is reduced by at least 20 percent. Preferable the residual dimer content in the ketone is reduced to 2 or more preferably 1 weight percent or less. Desirably the residual dimer content is reduced to less than 0.5 weight percent of said ketone.

Typically the peroxide is used in an amount of at least 0.5 weight percent of the mixture being treated (e.g. ketone, comonomers, diluent). Preferably, the amount of peroxide used is from 0.5 to 8 weight percent of said mixture; most preferably from about 1 to about 4 weight percent of said mixture. As the reaction is between the dimer and the peroxide, the rate of reaction will depend on the concentration of dimer and peroxide. If the concentrations of dimer and/or peroxide become very low the rate of reaction becomes prohibitively slow. For mixtures of pure ketone containing up to about 18 percent dimer 2 percent peroxide based on the weight of the composition being treated is an effective peroxide concentration. If, for example the dimer concentration were reduced with another monomer or diluent a corresponding increase in the peroxide concentration would be required. A limiting amount of peroxide, is when the peroxide concentration is such that the subsequent polymerization of the ketone cannot be controlled or when there is a danger or polymerization during treatment. At typical dimer concentrations from about 2 to 18 percent of the ketone, the ketone concentration should be at least 25 weight percent, more preferably about 60, most preferably about 75 weight percent of the monomer mixture being treated.

The temperature of the aging process may be from 0 to 45, preferably from 0 to 21 (room temperature) ° C. The time of treatment may be from 0.5 up to 50 hours; preferably less than 6 hours. Preferably the time of treatment is from about 3 to about 6 hours. The amount of peroxide, temperature and duration of treatment are all variables which will affect the degree of dimer removal from the ketone monomer. Appropriate conditions may be established by simple routine testing. It should be noted that the temperature may be varied during the treatment. For example the peroxide ketone mixture could be prepared at about room temperature (e.g. 20°-25° C.) and aged for 1 to 3 hours. Or the mixtures may be aged 1 hour, at room temperature (21° C.) then cooled to 0° to 5° C. and held for 3 to 6 hours.

After the ketone is treated as described above, it may subsequently be polymerized. The ketone may be homopolymerized or it may be copolymerized with an ethylenically unsaturated monomer. Suitable copolymerizable monomers include $C_{8-10}$ vinyl aromatic monomers which are unsubstituted or substituted by a $C_{1-4}$ alkyl radical or a chlorine atom; $C_{2-6}$ alkenyl nitriles; $C_{3-6}$ ethylenically unsaturated carboxylic acids; $C_{1-8}$ alkyl and hydroxyalkyl esters of $C_{3-6}$ ethylenically unsaturated carboxylic acids; and anhydrides of $C_{3-6}$ ethylenically unsaturated di-carboxylic acids.

Useful vinyl aromatic monomers include styrene and alpha methylstyrene. Useful nitriles include acrylonitrile and methacrylonitrile. Useful unsaturated carboxylic acids include acrylic acid, methacrylic acid; fumaric acid and itaconic acid. Suitable esters of ethylenically unsaturated carboxylic acids include methyl acrylate, ethyl acrylate, butyl acrylate, methyl methacrylate, ethyl methacrylate, and hydroxyethyl acrylate.

Suitable anhydrides of $C_{3-6}$ ethylenically unsaturated di-carboxylic acids include maleic anhydride.

The processes for polymerizing ethylenically unsaturated monomers are well known in the art and include thermal and free radical polymerization. The polymerization may be carried out in an aqueous emulsion in an organic solution, or in bulk. There is quite a comprehensive discussion of such polymerizations in the chapter "Polymerization of Alpha-beta-Unsaturated Carboxyl Compounds," (David M. Wiles) in the text Structure and Mechanism in Vinyl Polymerization T. Tsuruta and K. F. O'Driscoll, Marcel Dekker, Inc. New York, the text of which is herein incorporated by reference. It should be noted that the peroxides used to treat the ketones, may be also used to polymerize them. Thus, the ketones may be treated with all or a portion of the above disclosed peroxides and subsequently polymerized. It is also possible to treat the ketone with a mixture of one or more of the above peroxides and one or more additional non reactive peroxides such as t-butyl benzoyl peroxide or lauryl peroxide. Thus, it is possible to use mixed initiator systems to polymerize the ketone.

The following examples are intented to illustrate, but not limit, the invention. In the examples unless otherwise specified parts are parts by weight (e.g. grams).

EXAMPLE I

Styrene monomer in a glass vial was free radically polymerized at 88° C. with 0.0;0.25;0.5., and 1 weight percent of methyl isopropenyl ketone dimer which did not contain any inhibitor. The initiator was a mixed initiator comprising per 100 parts by weight of monomer 0.24 parts by weight of benzoyl peroxide and 0.06 parts by weight of tertiary butyl perbenzoate. The conversion of the styrene at 6 hours was determined. (e.g. the vials were opened; cooled to stop polymerization and the solids contents determined). A plot was made of conversion against MIPK dimer concentration. The results are shown in FIG. 1. FIG. 1 shows that MIPK dimer acts as a strong free radical polymerization inhibitor.

EXAMPLE II

A series of polymerizations were made of a

90:10 styrene/MIPK monomer and dimer mixture and a
95:5 styrene/MIPK monomer and dimer mixture.

In both cases the initiator was a mixture of benzoyl peroxide and tertiary butyl perbenzoate. The weight percent of initiator is set forth in Table I.

TABLE 1

| S/MIPK 95:5 | | | S/MIPK 90:10 | | |
|---|---|---|---|---|---|
| Benzoyl Peroxide | tert butyl per benzoate | Total | Benzoyl Peroxide | tert butyl per benzoate | Total |
| 0.24 | 0.06 | 0.30 | 0.24 | 0.06 | 0.30 |
| 0.36 | 0.09 | 0.45 | 0.40 | 0.10 | 0.50 |
| 0.48 | 0.12 | 0.60 | 0.56 | 0.14 | 0.70 |
| 0.60 | 0.15 | 0.75 | 0.72 | 0.18 | 0.90 |
| | | | 0.88 | 0.22 | 1.10 |
| | | | 1.04 | 0.26 | 1.30 |
| | | | 1.20 | 0.30 | 1.50 |
| | | | 1.36 | 0.34 | 1.70 |

The monomer mixtures were polymerized in glass vials at 88° C. At 6 hours the polymerizations were cooled to stop polymerization and the solids content in the vial was determined. The solids content was the conversion at 6 hours. A plot was made of the conversion at 6 hours against the total initiator concentration. This plot is shown in FIG. 2.

This data shows that 3 and 5 times as much initiator is required to obtain 100 percent conversion in systems with 5 and 10 weight percent MIPK than in pure styrene.

Figure 2:
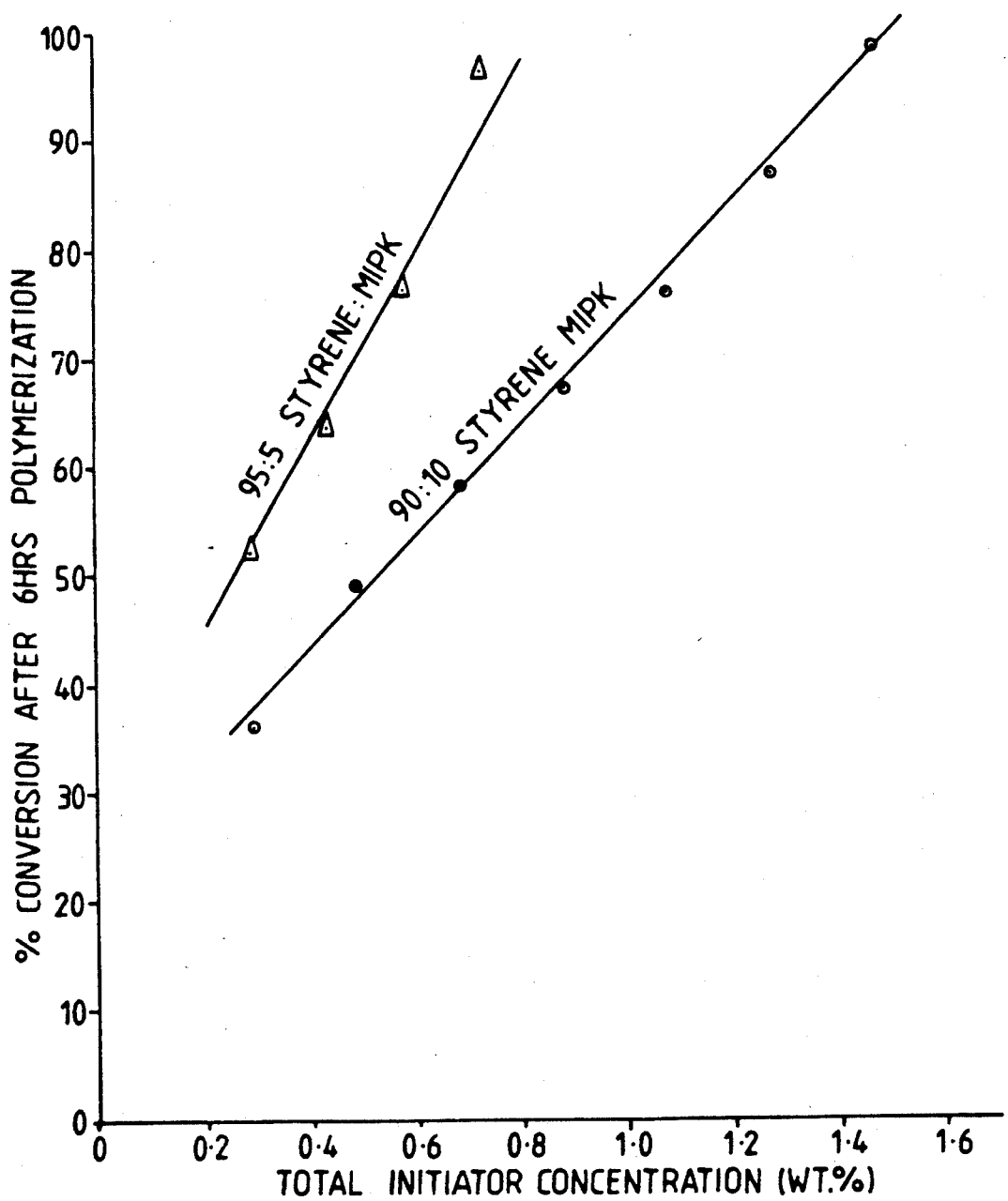
FIG. 2 is a plot of the percent conversion as a function of initial initiator concentration in 95:5 and 90:10 monomer mixtures of styrene and MIPK (containing dimer).

The data from FIG. 2 was used to calculate the initiator required for 100 percent conversion at various amounts of MIPK (e.g. 0, 5, and 10)

Figure 3:
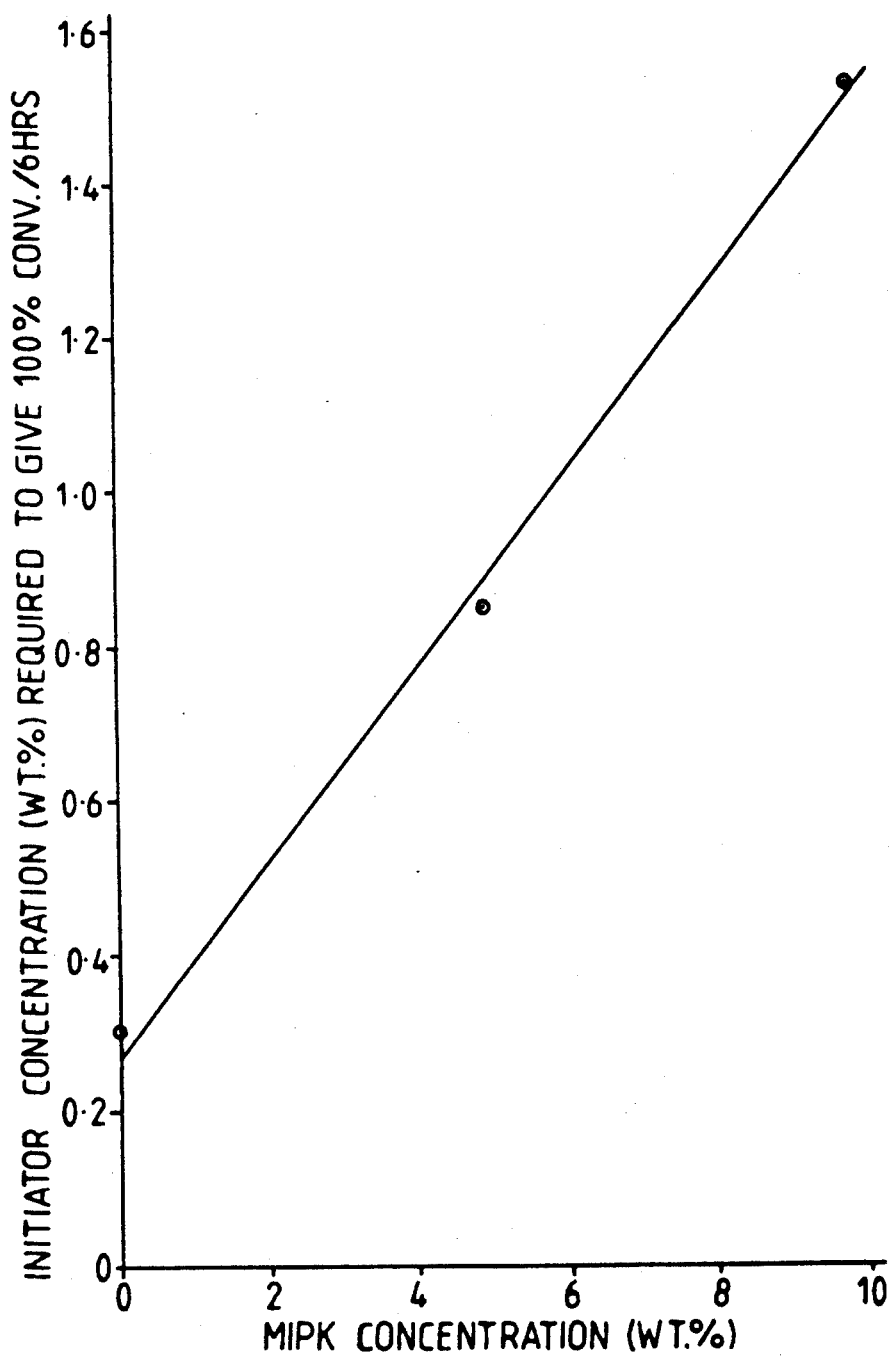
FIG. 3 is a plot of initiator concentration to obtain 100 percent conversion of a styrene MIPK (containing dimer) mixture at various MIPK concentrations.

This data was plotted in FIG. 3.

The MIPK used in the polymerization was analyzed and found to contain 8 percent dimer.

From this data the following empirical equation was derived.

$$I = 0.015\,[M_2][D_2] + 0.282$$

wherein

I is the required initiator concentration to achieve about 100 percent conversion in 6 hours,:

$M_2$ is the weight percent (based on the total monomers) of MIPK in the monomer mixture;

$D_2$ is the weight percent of dimer in MIPK.

From this equation the amount of initiator is not significantly increased for a polymer containing 5–10 weight percent MIPK if the dimer concentration is 2 weight percent or less. Obviously if the concentration of ketone, such as MIPK, used in the polymerization is greater then there should be a lower dimer content in the ketone. Thus, one should seek at least about a 20 percent reduction in dimer in the ketone in order obtain a reasonable rate of reaction without increased initiator concentration. Preferably the dimer concentration should be less than 2 desirably less than 1, most preferably less than 0.5 weight percent of ketone monomer.

EXAMPLE IIIA

Figure 4:
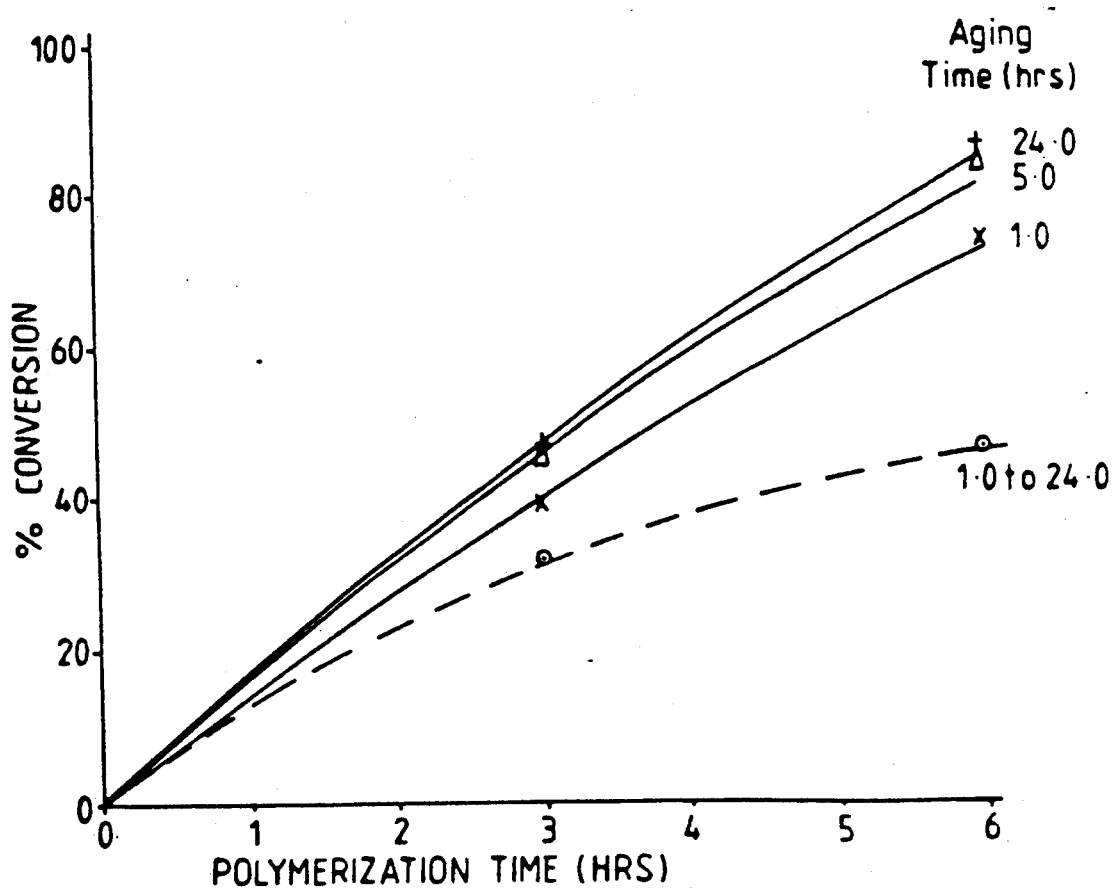
FIG. 4 is a plot of conversion against polymerization time for various treatments of styrene:MIPK (containing dimer) with benzoyl peroxide.

A series of vial copolymerizations of 95:5 styrene/MIPK carried out. The MIPK contained about 8 percent dimer. In one case all the styrene/MIPK and initiator (Benzoyl peroxide) were aged for various times before polymerization at 88° C. In the other cases mixtures of MIPK and part of the benzoyl peroxide initiator were aged then mixed with a comparably aged solution of styrene and remaining initiator immediately prior to polymerization. The aging was at 21° C. for 1 hour then for the specified time at 5° C. At 3 and 6 hours the solids of the polymerization system was determined. The data is set forth in Table II. For the different treatments conversion is plotted as a function of time in FIG. 4.

TABLE II

COPOLYMERIZATION OF STYRENE/MIPK AFTER VARIOUS PERIODS AND TYPES OF AGING.

| POLYMERIZATION RECIPES | | (1) | (2) | (3) | (4) | (5) | (6) |
|---|---|---|---|---|---|---|---|
| [A] | Styrene | 95.0 | 95.0 | 95.0 | — | — | — |
| | MIPK | 5.0 | 5.0 | 5.0 | — | — | — |
| | Benzoyl Peroxide | 0.3 | .03 | 0.3 | — | — | — |
| [B] | MIPK | — | — | — | 5.0 | 5.0 | 5.0 |
| | Benzoyl Peroxide | — | — | — | 0.1 | 0.1 | 0.1 |
| [C] | Styrene | — | — | — | 95.0 | 95.0 | 95.0 |
| | Benzoyl Peroxide | — | — | — | 0.2 | 0.2 | 0.2 |
| Aging Time Before Polymerization | | | | | | | |
| At 21° C. (hrs.) | | 1.0 | 1.0 | 1.0 | 1.0 | 1.0 | 1.0 |
| At 5° C. (hrs.) | | 0.0 | 4.5 | 23.0 | 0.0 | 4.5 | 23.0 |
| Solids After Polymerization (wt. %) | | | | | | | |
| 3 Hrs. | | 32.3 | 35.6 | 31.9 | 39.2 | 46.4 | 40.4 |
| 6 Hrs. | | 47.4 | 47.7 | 46.4 | 74.3 | 84.7 | 87.0 |
| Polymerization Temperature: | | | | 88° C. | | | |
| Polymerization Time: | | | | 6.0 Hrs. | | | |

The three solutions, [A], [B] and [C], were aged as shown above.

The polymerization vials were then charged according to the above amounts.

EXAMPLE IIIB

A monomer mixture was prepared comprising:
Styrene: 25
MIPK: 75 (containing about 8 percent dimer)
Benzoyl Peroxide: 1

The mixture was divided into two samples. One sample was aged for 2 hours at 22°. The second sample was aged 2 hours at 22° C. and 21 hours at 5° C. The samples were polymerized at 85° C. for 6 hours. The 6 hour solids for the samples aged at 22° C. only, was 21.6%, the 6 hour solids for the sample at 22° C. and 5° C. was 36.8%

From this data it can be seen that the process is most effective when aging the ketone in the presence of the peroxide and no further diluent or other monomers.

EXAMPLE IV

A sample MIPK and various amounts of benzoyl peroxide were aged for 1 hour at 22° C. and various times at 3° C. The samples were analyzed at various times at day 1, 2, and 3 for dimer content.

The results are set forth in Table III.

TABLE III

THE EFFECT OF AGING MIPK/ BENZOYL PEROXIDE ON MIPK COMPOSITION

| Sample Number | 1 | 2 | 3 |
|---|---|---|---|
| MIPK Lot 1051-1063 (Wt. %) | 100.00 | 99.0 | 98.0 |
| Benzoyl Peroxide (Wt. %) | 0.0 | 1.0 | 2.0 |
| Day 1 Results | | | |
| Time Aged | | | |
| 22° C. (Hrs.) | 1.0 | 1.0 | 1.0 |
| 3° C. (Hrs.) | 0.0 | 1.5 | 3.0 |
| MIPK (%) | 84.5 | 83.3 | 85.0 |
| MIPK Dimer (%) | 8.3 | 2.3 | 0.6 |
| MEK (%) | 3.2 | 2.9 | 3.0 |

TABLE III-continued
THE EFFECT OF AGING MIPK/BENZOYL PEROXIDE ON MIPK COMPOSITION

| Sample Number | 1 | 2 | 3 |
|---|---|---|---|
| MIPK Lot 1051-1063 (Wt. %) | 100.00 | 99.0 | 98.0 |
| Benzoyl Peroxide (Wt. %) | 0.0 | 1.0 | 2.0 |
| EVK (%) | 2.6 | 2.5 | 2.5 |
| Other (%) | 1.4 | 9.0 | 8.9 |
| Day 2 Results | | | |
| Time Aged | | | |
| 22° C. (Hrs.) | 1.0 | 1.0 | 1.0 |
| 3° C. (Hrs.) | 24.0 | 26.5 | 29.0 |
| MIPK (%) | 82.0 | 84.0 | 86.0 |
| MIPK Dimer (%) | 10.9 | 0.4 | 0.2 |
| MEK (%) | 2.8 | 3.1 | 3.0 |
| EVK (%) | 2.5 | 2.5 | 2.5 |
| Other (%) | 1.8 | 10.0 | 8.3 |
| Day 3 Results | | | |
| Time Aged | | | |
| 22° C. (Hrs.) | 1.0 | 1.0 | 1.0 |
| 3° C. (Hrs.) | 46.0 | 48.0 | 50.0 |
| MIPK (%) | 82.1 | 85.6 | 84.1 |
| MIPK Dimer (%) | 10.9 | 0.3 | 0.2 |
| MEK (%) | 2.8 | 2.9 | 2.9 |
| EVK (%) | 2.5 | 2.5 | 2.5 |
| Other (%) | 1.7 | 8.7 | 10.3 |
| Solids (wt. %) | 0.0 | 0.34 | 0.77 |

These results show that at 1 or 2 percent benzoyl peroxide aging at about 49-51 hours produces substantially similar reductions in dimer.

Significant reductions in dimer content may be obtained in from 2.5 to 3 hours at 3° C. using 1 to 2 weight percent benzoyl peroxide (based on the MIPK). Clearly significant reductions in dimer level are achievable in accordance with the present invention.

EXAMPLE V

A series of polymerizations of 95 parts of styrene and 5 parts of various ketone monomers was carried out. In the A series the ketone monomer and 0.1 parts of initiator were aged at 3° C. This solution was mixed with a solution of styrene and 0.2 part of initiator, which had been aged at 3° C. for the same amount of time. The two aged solutions were mixed immediately prior to polymerization, and polymerized. In the B series of experiments the ketone, styrene and initiator were mixed together and aged at 3° C. for the specified period of time, then polymerized. The solids at various times was measured. Additionally the dimer content in the ketone was measured before and after aging, of the peroxide in the ketone monomer only.

The ketone, initiator, aging time, 6 hour solids and dimer content are set forth in Table IV.

EXAMPLE VI

In a manner similar to example V mixtures of 90:5:5 Styrene:ACN:MIPK were polymerized. The initiator was Benzoyl peroxide. The samples were aged as described in Example V for 20 hours. The polymerization temperature was 85° C. The 6 hours solids was 100 percent for the sample prepared by aging the MIPK and 0.1 parts of peroxide. The 6 hour solids for aging the entire reaction mixture was 66.4 percent. The dimer content before aging with peroxide was 10.4 and 0.7 after aging.

TABLE IV

| | A | B | A | B | A | B | A | B | A | B | A | B | A | B |
|---|---|---|---|---|---|---|---|---|---|---|---|---|---|---|
| Initiator | | | | | | | | | | | | | | |
| t-butyl perbenzoate | 0.3 | 0.3 | | | | | | | 0.06 | 0.06 | | | | |
| Lauroyl peroxide | | | 0.3 | 0.3 | | | | | | | | | | |
| Azobisobutyronitrile | | | | | 0.3 | 0.3 | | | | | | | | |
| t-butyl hydroperoxide | | | | | | | 0.3 | 0.3 | | | | | | |
| benzoyl peroxide | | | | | | | | | 0.24 | 0.24 | 0.3 | 0.3 | 0.3 | 0.3 |
| ketone-MIPK | X | X | X | X | X | X | X | X | X | X | X | X | | |
| -Methyl vinyl ketone (MVK) | | | | | | | | | | | | | X | X |
| Polymerization Temp. °C. | 95 | 95 | 75 | 75 | 75 | 75 | 105 | 105 | 85 | 85 | 85 | 85 | 85 | 85 |
| Aging time (hrs.) | 19 | 19 | 19 | 19 | 19 | 19 | 21 | 21 | 19 | 19 | 20 | 20 | 20 | 20 |
| 6 hrs. solids | 44.9 | 44.2 | 28.4 | 29.2 | 61.9 | 60.2 | 56.5 | 51.8 | 62.0 | 45.0 | 94.0 | 50.6 | 82.2 | 65 |
| Dimer Content | | | | | | | | | | | | | | |
| before aging | 10.4 | 10.4 | 10.4 | 10.4 | 10.4 | 10.4 | 10.4 | 10.4 | 10.4 | 10.4 | 10.4 | 10.4 | 5.8 | 5.8 |
| after aging | 10.1 | | 9.3 | | 9.9 | | 10.5 | | 0.8 | | 0.8 | | 0.03 | |

X = means the ketone is present.

EXAMPLE VII

In a manner similar to Example V a mixture of 95:10:5 styrene:methyl methacrylate:MIPK was polymerized. The initiator was benzoyl peroxide. The samples were aged as described in example V for 21 hours. The polymerization temperature was 85° C. The 6 hours solids for the sample prepared by aging the MIPK and 0.1 parts benzoyl peroxide before polymerization was 93.4 percent. The 6 hours solids for the sample prepared by aging the entire reaction mixture before polymerization was 57.4 percent. The initial dimer concentration was 10.4 percent and the dimer concentration in the aged solution of MIPK and benzoyl peroxide was 0.7 percent. Examples V, VI and VII show that free radical initiators other than those which contain an aromatic nucleus do not "reduce" the dimer content in alpha beta ethylenically unsaturated ketones. The experiments also confirms the conclusion reached in Experiment III. Additionally, the experiments show that the process may be used with a number of copolymerizable monomers such as methyl methacrylate and acrylonitrile.

EXAMPLES VIII

A 2 weight percent solution of 2,5-dimethyl-2,5-bis(-benzyl peroxy) hexane [Lupersol 118 (trademark)]was prepared in methyl isopropenyl ketone (MIPK). The sample was aged 20 hours at room temperature. The dimer content of MIPK at zero and at 20 hours was measured. At zero the dimer content was 10.4 percent. At 20 hours the dimer content was 7.7 percent. This shows about a 20 percent reduction in dimer content as a result of the treatment.

We claim:

1. A method for reducing the dimer content in a liquid mixture consisting essentially of:
one or more monomers of the formula

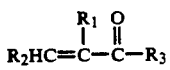

wherein
R$_1$ is a hydrogen atom or a C$_{1-4}$ alkyl radical;
R$_2$ is a hydrogen atom or a C$_{1-4}$ alkyl radical; and
R$_3$ is a C$_{1-4}$ alkyl radical or a C$_{6-10}$ aromatic radical; and
dimers thereof;
which comprises contacting said mixture with at least one or more peroxides selected from the group consisting of:
(i) benzoyl peroxide; and
(ii) peroxides of the formula

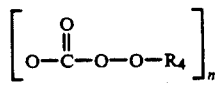

wherein R$_4$ is a C$_{1-6}$ branched or straight chain alkyl radical or a C$_{6-10}$ aromatic radical and n is 1 or 2; at a temperature from 0° C. to 45° C. and for a period of time so that the weight percent of residual dimer in said mixture is reduced by at least 20 percent.

2. A method according to claim 1 wherein the amount of peroxide is at least 0.5 weight percent of said mixture.

3. A method according to claim 2 wherein the time of said treatment is from 0.5 to 50 hours.

4. A method according to claim 3 wherein said peroxide is present in an amount from 0.5 to 8 weight percent of said mixture.

5. A method according to claim 4 wherein the time of said treatment is less than 6 hours.

6. A method according to claim 5 wherein said one or more monomers are selected from the group consisting of, methyl vinyl ketone, ethyl vinyl ketone, propyl vinyl ketone, isopropyl vinyl ketone, butyl vinyl ketone, methyl isopropenyl ketone, ethyl isopropenyl ketone, phenyl vinyl ketone and phenyl isopropenyl ketone.

7. A method according to claim 6 wherein said peroxide is selected from the group consisting of benzoyl peroxide and 2,5-dimethyl-2,5-bis(benzoyl peroxy) hexane.

8. A method according to claim 7 wherein the weight percent of residual dimer in said mixture is 1 weight percent or less.

9. A method according to claim 8 wherein said one or more monomers are selected from the group consisting of: methyl vinyl ketone and methyl isopropenyl ketone.

10. A method according to claim 9 wherein said peroxide is benzoyl peroxide.

11. A method according to claim 10 wherein the temperature is from 0° to 21° C.

12. A method according to claim 11 wherein said benzoyl peroxide is present in an amount from about 1 to 2 weight percent of said mixture.

13. A method according to claim 12 wherein the residual dimer is present in an amount of 1.0 weight percent or less of said mixture.

14. A method according to claim 13 wherein the residual dimer is present in an amount of 0.5 weight percent or less of said mixture.

15. A method according to claim 8 further sequentially comprising homopolymerizing said ketone.

16. A method according to claim 14 further sequentially comprising homopolymerizing said ketone.

17. A method according to claim 8 further sequentially comprising copolymerizing said ketone with one or more monomers selected from the group consisting of C$_{8-10}$ vinyl aromatic monomers which are unsubstituted or substituted by a C$_{1-4}$ alkyl radical or a chlorine atom; C$_{2-6}$ alkenyl nitriles; C$_{3-6}$ ethylenically unsaturated carboxylic acids; C$_{1-8}$ alkyl and hydroxyalkyl esters of C$_{3-6}$ ethylenically unsaturated carboxylic acids, and anhydrides of C$_{3-6}$ ethylenically unsaturated dicarboxylic acids.

18. A method according to claim 14 further sequentially comprising copolymerizing said ketone with one or more monomers selected from the group consisting of C$_{8-10}$ vinyl aromatic monomers which are unsubstituted or substituted by a C$_{1-4}$ alkyl radical or a chlorine atom., C$_{2-6}$ alkenyl nitriles; C$_{3-6}$ ethylenically unsaturated carboxylic acids; C$_{1-8}$ alkyl and hydroxyalkyl esters of C$_{3-6}$ ethylenically unsaturated carboxylic acids, and anhydrides of C$_{3-6}$ ethylenically unsaturated dicarboxylic acids.

19. A process according to claim 18 wherein one or more monomers are selected from the group consisting of: styrene, alpha methyl styrene, acrylonitrile, methacrylonitrile, acrylic acid, methacrylic acid, fumaric acid, itaconic acid, methyl acrylate, ethyl acrylate, butyl acrylate, methyl methacylate, ethyl methacrylate, hydroxyethyl acrylate and maleic anhydride.

* * * * *